United States Patent
Anumalasetty et al.

(10) Patent No.: US 10,020,076 B1
(45) Date of Patent: Jul. 10, 2018

(54) PERSONAL ASSISTANT COMPUTING SYSTEM MONITORING

(71) Applicant: International Business Machines Corporation, Armonk, NY (US)

(72) Inventors: Kiran K. Anumalasetty, Bangalore (IN); Phani Kumar V. U. Ayyagari, Hyderabad (IN); Manish A. Bhide, Hyderabad (IN)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/840,225

(22) Filed: Dec. 13, 2017

Related U.S. Application Data

(63) Continuation of application No. 15/729,832, filed on Oct. 11, 2017.

(51) Int. Cl.
| | |
|---|---|
| *G16H 50/20* | (2018.01) |
| *G06F 19/00* | (2018.01) |
| *G16H 15/00* | (2018.01) |
| *G10L 15/08* | (2006.01) |
| *G10L 15/02* | (2006.01) |
| *G10L 15/05* | (2013.01) |

(52) U.S. Cl.
CPC ............ *G16H 50/20* (2018.01); *G06F 19/345* (2013.01); *G06F 19/3487* (2013.01); *G16H 15/00* (2018.01); *G10L 15/02* (2013.01); *G10L 15/05* (2013.01); *G10L 15/083* (2013.01)

(58) Field of Classification Search
CPC ..................... G06F 19/345; G06F 19/3487
See application file for complete search history.

(56) References Cited

U.S. PATENT DOCUMENTS

| | | | |
|---|---|---|---|
| 6,093,158 A | 7/2000 | Morris | |
| 7,914,468 B2 | 3/2011 | Shalon et al. | |
| 2014/0200463 A1 | 7/2014 | el Kaliouby et al. | |
| 2015/0313529 A1* | 11/2015 | Nevo | A61B 5/165 600/595 |
| 2016/0110523 A1* | 4/2016 | Francois | G06Q 50/24 705/2 |
| 2016/0292585 A1 | 10/2016 | Kozloski et al. | |
| 2016/0317781 A1 | 11/2016 | Proud | |
| 2017/0262604 A1 | 9/2017 | Francois | |

OTHER PUBLICATIONS

El Kaliouby et al., "The Mood-Aware Internet of Things," Affectiva blog, Jul. 24, 2015, 5 pages. http://blog.affectiva.com/the-mood-aware-internet-of-things.

(Continued)

*Primary Examiner* — Linh Giang Le
(74) *Attorney, Agent, or Firm* — Nicholas D. Bowman

(57) ABSTRACT

A computing system is configured to process at least one voice input of a user and output an audio result. The computing system comprises at least one microphone configured to receive the voice input from the user. The computing system further comprises at least one processor configured to at least interpret the voice input and generate the audio result. The computing system also comprises an output speaker device configured to output the audio result. The audio result includes a description of whether one or more behavioral health states associated with the user have been detected.

1 Claim, 10 Drawing Sheets

(56) References Cited

OTHER PUBLICATIONS

"ODH, Inc. and IBM Watson Health Introduce Menthes™, a Population Health Management Platform to Transform Behavioral Healthcare," IBM News releases, Apr. 20, 2016, 2 pages. http://www-03.ibm.com/press/us/en/pressrelease/49564.wss.

Helgadottir, F., "The Future of Computerized Therapy," PsychCentral, May 17, 2016, pp. 1-3. https://psychcentral.com/lib/the-future-of-computerized-therapy/.

"Overcome social anxiety," AI Therapy, printed Apr. 25, 2017, 2 pages. https://www.ai-therapy.com/.

"Google Home," printed Oct. 10, 2017, 3 pages. https://store.google.com/us/product/google_home.

"Echo," Amazon.com, printed Oct. 10, 2017, 12 pages. https://www.amazon.com/dp/B07456BG8N?tag=googhydr-20
&hvadid=223605111254&hvpos=1t1&hvnetw=g
&hvrand=16353498098771959865&hvpone=&hyptwo=
&hvqmt=e&hvdev=c&hvdvcmdl=&hvlocint=
&hvlocphy=9019794&hvtargid=kwd-295921611050
&ref=pd_sl_2g7cb1h5ze_e.

Anumalasetty et al., "Personal Assistant Computing System Monitoring", U.S. Appl. No. 15/729,832, filed Oct. 11, 2017.

IBM, List of IBM Patents or Patent Applications Treated as Related, Dec. 12, 2017, 2 pages.

* cited by examiner

PERSONAL ASSISTANT COMPUTING SYSTEM MONITORING

BACKGROUND

This disclosure relates generally to personal assistant computing systems, and more specifically to receiving sensor data input corresponding to one or more attributes of a user and outputting one or more results based on analyzing the sensor data.

Personal assistant computing systems are configured to receive user input (e.g., a voice command) and provide a corresponding output response based on the input received. QA systems, for example, receive input questions, analyze them, and return applicable candidate answers in order to answer the input questions. QA systems and other personal assistant computing systems can rely on advanced computing techniques such as natural language processing in order to output a result response. QA systems may provide mechanisms for searching very large sources of content and analyze the content with regard to a given input question in order to determine an answer to the question. In some QA systems this may take the form of hypothesis generation, scoring, and ranking to determine a final set of one or more output answers. In order to search these very large sources of content and quickly process data, some personal assistant computing systems include dozens of servers, each of which include thousands of processor cores (e.g., 2, 870) and a large quantity of random access memory (RAM) (e.g., 16 terabytes). Such personal assistant computing systems can process around 500 gigabytes—the equivalent of a million books—per second.

SUMMARY

One or more embodiments are directed to a computer-implemented method, a computing system, and a computer program product. In some embodiments, a computing system is configured to process at least one voice input of a user and output an audio result. The computing system may also include at least one microphone configured to receive the voice input from the user. The computing system may further include at least one processor configured to at least interpret the voice input and generate the audio result. The computing system may also include an output speaker device configured to output the audio result. The audio result may include a description of whether one or more behavioral health states associated with the user have been detected.

In some embodiments, a computer program product comprises a computer readable storage medium having program code embodied therewith. The program code may be executable/readable by a computing device to receive a user request to download one or more health plugins. The one or more health plugins may correspond to one or more respective user health states that will be monitored. In response to the downloading of the one or more health plugins, one or more sensor devices may be registered. The one or more sensor devices may be for use in measuring one or more health attributes of the user. One or more output devices may also be registered. The one or more output devices may be activated in response to the one or more respective user health states being detected. The activation of the one or more output devices may help to remedy or cope with the one or more respective user health states that the user is experiencing.

In yet other embodiments, a computer-implemented method comprises receiving, over one or more computing networks and from one or more devices, a first set of sensor data corresponding to one or more behavioral attributes of a user. It may be determined, via a processor-based inference technique and based on analyzing the first set of sensor data, that at least one of the one or more behavioral attributes indicates one or more emotional or mental states of the user. At least one trigger estimate may be generated, via a predictive technology method. The generating of the trigger estimate may include identifying one or more variables as at least one potential cause for why the user is in the one or more emotional or mental states.

Figure 1:
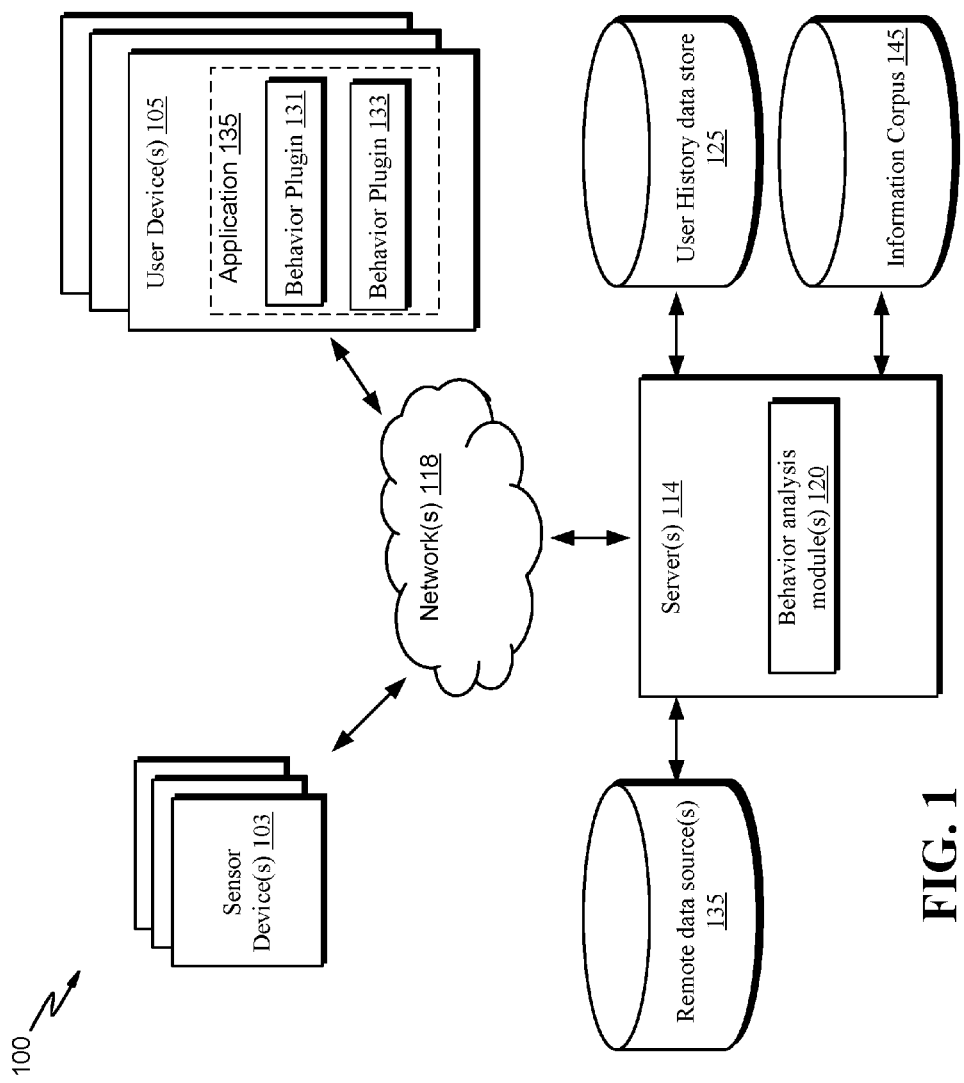
FIG. 1 is a block diagram of a computing environment, according to embodiments.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

Aspects of the present disclosure relate to receiving sensor data corresponding to one or more attributes of a user and outputting a result based on analyzing the sensor data. While the present disclosure is not necessarily limited to such applications, various aspects of the disclosure may be appreciated through a discussion of various examples using this context.

Some personal assistant computing systems are configured to return an auditory output result in response to an auditory user command or question. These personal assistant computing systems are designed to allow the user to issue a voice-activated query and receive an auditory response with little to no physical manipulation, attention, or interaction by the user. For example, smart speakers, such as GOOGLE HOME (designed by ALPHABET), and AMAZON ECHO (designed by AMAZON) have been developed. These smart speakers include one or more microphones to receive an auditory user input command, one or more transceivers to communicate with one or more servers to help generate a response, and one or more speakers to output the response to answer the user's command. These smart speakers are often located in peoples' homes and help perform various automated tasks without physical user involvement such as turn on the living room lights, answer a question, etc. Accordingly, without the user physically interacting with a mouse, keyboard, touchpad, switch, etc., the user may issue an auditory command and receive an automated response all while performing some unrelated physical task.

These smart speaker systems as well as other personal assistant computing systems may fail to monitor and analyze behavioral or other health aspects of a user in real time or near real time and give the user a more complete assistance experience. The present disclosure consequently recognizes that it may be beneficial to monitor and analyze this data via these unique systems. However, such monitoring and analyzing health data within these systems can involve complex sensor data aggregation and non-intuitive or non-conventional processing methods. It also involves seamless and sophisticated coordination between each component of these systems, as described in more detail below. Accordingly, embodiments of the present disclosure improve current personal assistant computing system technology. For example, some embodiments improve existing personal assistant computing system technology by at least receiving, over a computing network and from one or more devices, sensor data corresponding to one or more behavioral attributes of a user; determining, via a processor-based inference technique and based on analyzing the sensor data, that at least one of the one or more behavioral attributes indicates one or more emotional or mental states of the user; and/or generating, via a predictive technology method, at least one trigger estimate, the generating of the trigger estimate includes identifying one or more variables as at least one potential cause for why the user is in the one or more emotional or mental states.

Many people experience various health and wellness issues and desire greater assistance for coping with or remedying these issues. Many individuals, for example, seek out emotional and behavioral wellness remedies. In an illustrative example, people with depression, anxiety disorders, anger, etc. may seek behavioral healthcare programs like psychotherapy, counseling, or cognitive behavioral therapy (CBT). Typically, these programs require a lot of manual monitoring by both a health care practitioner and a patient. For example, a person on an anger management treatment plan may have to monitor their anger, identify triggers or variables that cause or are associated with the person's anger, and remedy the anger. There are many challenges with this. First, it may be difficult for a non-health care practitioner to identify what variable(s) are associated with the anger, particularly where such variable(s) often occur outside the presence of a healthcare practitioner. This may in turn make it difficult to remedy the problem. Further, it may be arduous for a patient to continuously monitor his/her behavior. Moreover, manual monitoring may cause a healthcare professional or patient to inaccurately determine that there is a problem. Embodiments of the present disclosure address some or all of these challenges as described in more detail below. Some embodiments thus automate health evaluation and treatment (which was previously performed by a human healthcare professional) by receiving sensor data and by using various specific rules and data sources to identify and potentially remedy a particular health issue and its associated triggers.

FIG. 1 is a block diagram of a computing environment 100, according to embodiments. The computing environment 100 includes one or more user devices 105, one or more sensor devices 103, and one or more servers 114, each of which are communicatively coupled (e.g., via one or more networks 118) with each other. In some embodiments, the computing environment 100 is implemented within a cloud computing environment, or use one or more cloud computing services. Consistent with various embodiments, a cloud computing environment includes a network-based, distributed data processing system that provides one or more cloud computing services. Further, a cloud computing environment may include many computers, hundreds or thousands of them or more, disposed within one or more data centers and configured to share resources over the network 118. For example, the server(s) 114 may be part of a cloud computing system.

Figure 10:
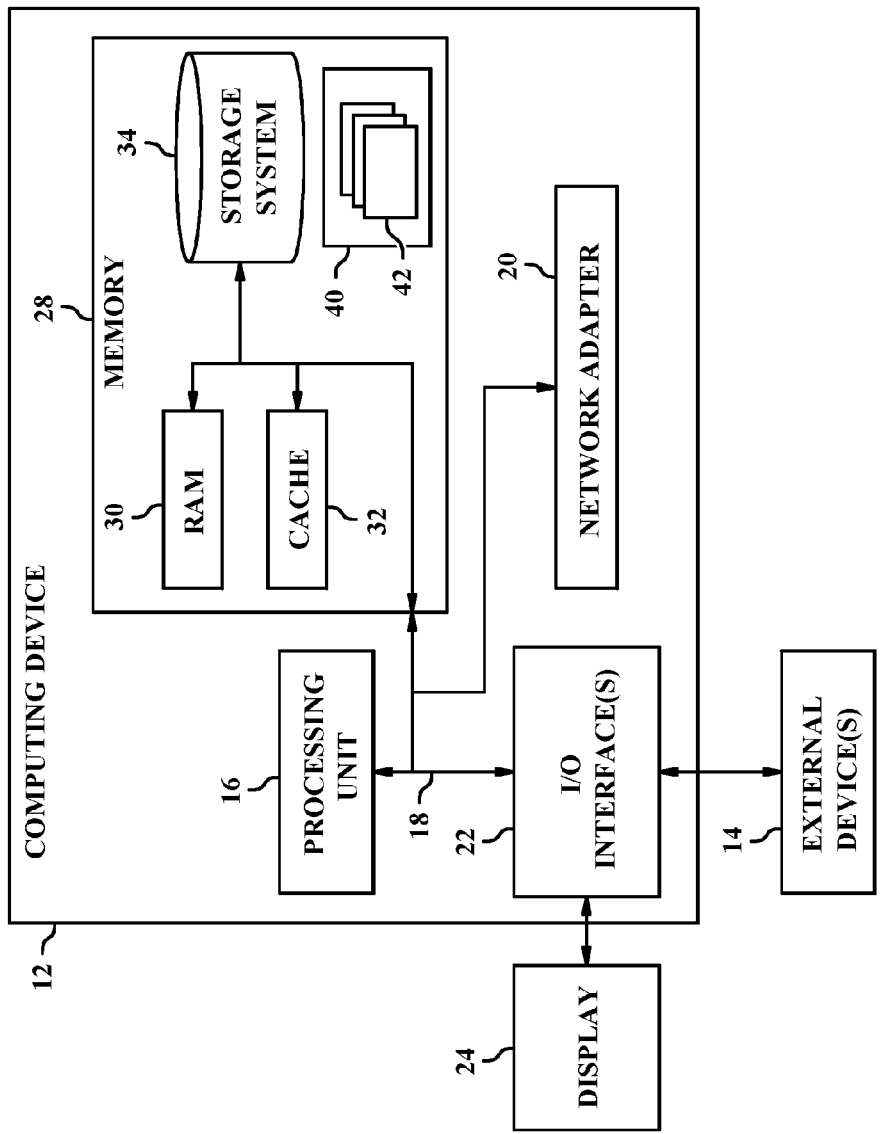
FIG. 10 is a block diagram of a computing device, according to embodiments.

Consistent with some embodiments, the user device(s) 105, the sensor device(s) 103, and/or the server(s) 114 are configured the same as or analogous to the computing device 12 as illustrated in FIG. 10. In some computing environments, more or fewer components may be present than illustrated in FIG. 1. For example, the computing environment 100 may not include the information corpus 145 or the remote data source(s) 135.

The user device(s) 105 and/or the sensor device(s) 103 establish a connection or communicates with the server(s) 114 and/or each other via the network(s) 118. Network(s) 118 is or includes any suitable network such as a local area network (LAN), a general wide area network (WAN), a personal area network (PAN), and/or a public network (e.g., the internet). For example, in some embodiments, the sensor device(s) 103 communicates or sends data to the user device(s) 105 via a PAN (e.g., Bluetooth®, as developed by Bluetooth Special Interest Group (SIG)). In some embodiments, upon receiving information from the sensor device(s) 103, the user device(s) 105 communicates or transmits data to the server(s) 114 via a WAN. Alternatively, the sensor device(s) 103 and/or the user device(s) 105 may communicate directly with the server(s) 114 (e.g., via a WAN). The server(s) 114 may responsively send data to or communicate to the user device(s) 105 and/or the sensor device(s) 103.

The sensor device(s) 103 include one or more sensors that measures, identifies, and/or detects certain event(s) in a physical environment based on an input. In some embodiments, the sensor device(s) 103 measures behavior or particular attributes of a user in order to assess that user's health. For example, the sensor device(s) 103 may be or include a microphone to measure a decibel level of a user's voice; an accelerometer configured to measure movements of a user; a surveillance camera to assess activities of the user, etc. In some embodiments, the sensor device(s) 103 are computing devices that include sensor(s). In other embodiments, the sensor device(s) are stand-alone sensor(s).

The user device(s) 105 are or include any device(s) that a user typically interfaces with, such as a mobile phone, a smart watch, a smart speaker, a television, a thermostat, a light switch system, and/or any other suitable device. In some embodiments, the user device(s) 105 include the sensor device(s) 103. For example, the user device(s) 105 may be or include a smart speaker and the smart speaker may include various sensor devices, such as a microphone, a surveillance camera, etc. Accordingly, in these embodiments, at least some of the user device(s) 105 and the sensor device(s) 103 communicate with each other or transmit signals via a local physical connection, as opposed to a remote network-based connection. In some embodiments, as illustrated in FIG. 1, the user device(s) 105 include one or more computing devices (e.g., a mobile device) that includes the application 135. In some embodiments, if there are two or more user devices 105 (and/or sensor devices 103), some or each of these devices may also establish a wireless connection and communicate with each other via a network.

The application 135 includes the behavior plugins 131 and 133. In particular embodiments, the user downloads particular service parameters to the application 135 that the user already employs (e.g., SPOTIFY, GOOGLE CALENDER, etc.) and other configurations (e.g., control timers, set up custom alerts, etc.) such that a particular server of the server(s) 114 knows what service to contact or output to generate upon a particular user request. The behavior plugins 131 and 133 are individual add-ons or modules within the application 135 (e.g., that is installed on a mobile device) that are utilized to set individual parameters for a particular behavior. For example, behavior plugin 131 may be an "anger management" plugin and behavior plugin 133 may be an "obsessive compulsive disorder" plugin. In an example illustration for the anger management plugin, the user may register, configure, or set up particular sensor device(s) 103 or other devices (e.g., PHILIPS HUE, ROBO-VAC, smart surveillance systems, smart speakers, etc.) such that the behavior analysis module(s) 120 knows which sensor data to analyze from the sensor device(s) 103 that will be a means to detect anger. Further, through the registration, the behavior analysis module(s) 120 may know which devices to transmit an output to, as described in more detail below.

Staying with the anger management illustration, the user and/or user's doctor may also register tailored services to query and/or input patient record data to help assess the user's anger levels. For example, a user's doctor may upload any words, phrases, and/or actions that a user typically presents with that always leads to his/her particular anger. In some embodiments, users' schedules or other unique information (e.g., entire patient records) associated with particular behavior plugins may be uploaded.

The behavior analysis module(s) 120 performs various functions, calculations, and analyses as described in more detail below. Each of these behavior analysis modules 120 may ultimately detect, monitor, and/or analyze a particular user behavior, infer one or more health states of the user, and cause a response output to be made based on one or more policies, rules and/or data received from the detecting and monitoring. For example, behavior analysis module(s) 120 may correspond to an "anger" module that detects and analyzes the user's anger, and provides output responses. In some embodiments, the user device(s) 105 and/or the sensor device(s) 103 include the behavior analysis module(s) 120 in addition to or instead of the server(s) 114. As disclosed herein, "health state" refers to any health condition or health event episode. For example, a health state may refer to one or more mental, physical, and/or emotional health events. In an illustrative example, a mental or emotional health state includes obsessive-compulsive disorder, anger disorder, acute stress disorder, major depressive disorder, posttraumatic stress disorder, generalized anxiety disorder, and simple phobia.

The server(s) 114 are one or more computing devices that are associated with executing requests from the application 135 and/or the sensor device(s) 103 over the network(s) 118. A developer may design the application 135 that is configured to communicate to at least one of the server(s) 114 in order to obtain or analyze a particular set of data. In some embodiments, the server(s) 114 includes a first central server that directly communicates with the user device(s) 105 and/or the sensor device(s) 103 and a second server or set of servers (e.g., a web server) that communicates with the central server and/or user device(s) 105. When the user issues a command or phrase, the phrase may be routed to the central server API and then to the second web server API corresponding to the need.

The user history data store 125 includes data associated with a user such as user name, user calendaring data, user health history, a sampling history made by the sensor device(s) 103 (e.g., a year's worth of data from a surveillance system), social media posts of the user, user preferences (e.g., music, food, games), user's registered behavior plugin information, user's registered devices, user's registered services, etc. In some embodiments, the user history data store 125 includes data that describes past learned triggers or variables and behavioral episodes, which is described in more detail below.

The remote data source(s) 135 includes data that the server(s) 114 query over a wireless network in order to analyze the sensor data and output an appropriate response. For example, a first server of the server(s) 114 may query an API of a second server of the server(s) 114 in order to retrieve data from the second server that the first server needs to output an appropriate response. The second server may contain data that specifies particular remedies or coping mechanisms for a particular behavior that the first server needs as an output to provide back to the user device(s) 105.

The information corpus 145 includes unstructured and/or structured data for use in analyzing by the behavior analysis module(s) 120 and providing an appropriate output. For example, structured data includes data from a database, whereas unstructured data includes data such as electronic books, journals, social media passages, blogs, electronic newspapers, etc. In these embodiments, natural language processing (NLP) is utilized to parse these unstructured data into meaningful data to help analyze the sensor data and provide an appropriate response, as described in more detail below.

In some embodiments, the information corpus 145 instead or in addition includes health state models or templates that are compared against readings from the sensor device(s) 103 in order to determine whether the readings violate the policies/rules and/or exceed a threshold. In some embodiments, the policies and rules are static such that model data is retrieved from the remote data source(s) 135 to determine policies for all users. In some embodiments, instead or in addition to the static policies, the policies include dynamic models such that a particular user and/or the user's doctor can set the policies/rules specific to the particular user's idiosyncratic needs (e.g., a user always gets mad when driving so anytime a user drives, this may violate a policy and a notification may be sent to the user).

FIG. 1 illustrates at least that a user's health is monitored and output responses may be responsively generated. For example, a user may download or activate the application 135 and/or a device (e.g., a smart speaker). In some embodiments, the sensor device(s) 103 may then measure various user behavior (e.g., movement, text messages, images, noise levels) and transmit this sensor data to the server(s) 114. The behavioral analysis module(s) 120 may then help determine whether one or more units of the sensor data exceeds a threshold(s) or violates certain policy criteria corresponding to a health state. In order to make this determination, the behavior analysis module(s) 120 may retrieve data from the remote data source(s) 135, the user history data store 125, and/or the information corpus 145. In response to this determining by the behavior analysis module(s) 120, the server(s) 114 may then responsively transmit data to the user device(s) 105, such as a smart speaker, indicating that a certain behavior of the user has been detected and that the user should perform some responsive action (e.g., take deep breaths, exercise, take medication, etc.). In other examples, the user device(s) 105 may be or include some external device that is modified in some way in response to the determining that some behavioral policy has been violated. For example, in response to the user's behavior surpassing a threshold, the behavior analysis module(s) 120 may transmit a signal (e.g., via the network(s) 118) to the user device(s) 105, which is configured to cause a device to play a particular song, play a particular movie on a television, turn a thermostat to a particular setting, etc. based on the behavior monitored.

Figure 2:
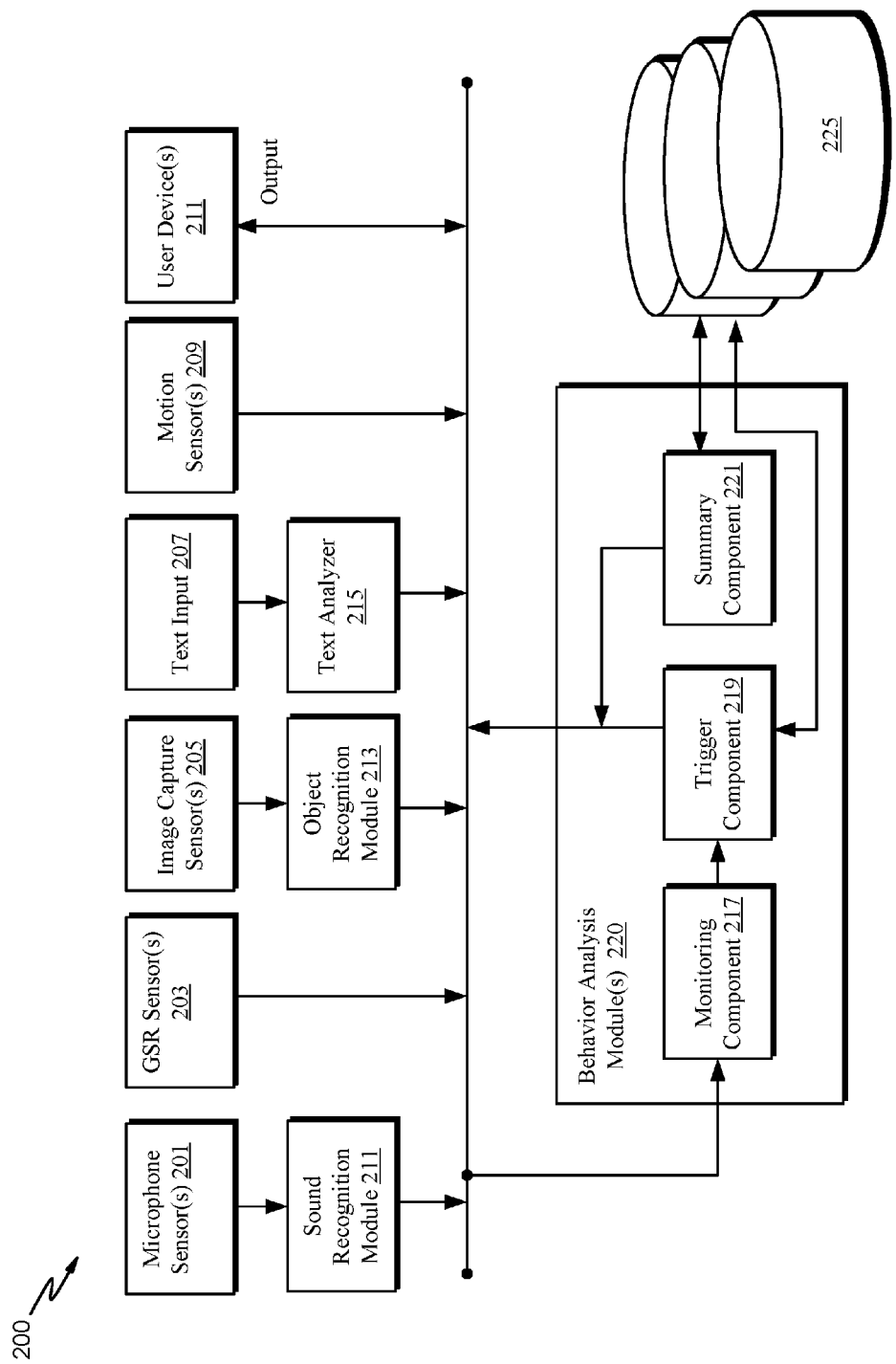
FIG. 2 is a block diagram of a computing environment that illustrates the analyzing of sensor data, according to embodiments.

FIG. 2 is a block diagram of a computing environment 200 that illustrates the analyzing of sensor data, according to embodiments. The computing environment 200 includes the microphone sensor(s) 201, a sound recognition module 211, Galvanic Skin Response (GSR) sensor(s) 203, image capture sensor(s) 205 (e.g., a surveillance h), an object recognition module, text input 20 (e.g., one or more characters received from a text message), a text analyzer 215, motion sensor(s) 209 (e.g., an accelerometer), user device(s) 211, a behavior analysis module(s) 220, and one or more data sources 225. The behavior analysis module(s) 220 includes a monitoring component 217, a trigger component 219, and a summary component 221.

In some embodiments, some or each of the sensors in FIG. 2—microphone sensor(s) 201, GSR sensor(s) 203, image capture sensor(s) 205, text input 207, and motion sensor(s) 209—are the sensor device(s) 103 as illustrated in FIG. 1. It is recognized by one of ordinary skill in the art that the sensors shown in FIG. 2 are illustrative only. Accordingly, for example, there may be more or less sensors. In an illustrative example, more sensors may be included, such as a pulse oximeter sensor configured to for measuring oxygen saturation levels, heart rate, and respiration rate, of a person.

The microphone sensor(s) 201 measure sound levels and sound variations within a particular environment. Sound is defined by pressure variations. Pressure may first be converted (e.g., from electrical analogue signal(s) via a pressure transducer) to digital noise signal(s) and one or more values of the digital data is obtained for measuring. These digital values are then passed to the sound recognition module 211. The sound recognition module 211 may perform any suitable technique(s) for recognizing and interpreting the output of the microphone sensor(s) 201. In some embodiments, the digital signals(s) measured by the microphone sensor(s) 201 are divided into small segments (e.g., 3 hundredths of a second). The sound recognition module 211 then matches these small segments to a first set of known phonemes in a particular language, such as English. The Sound recognition module 211 then analyzes and compares these first set of phonemes with each other. These first set of phonemes are then plotted through a complex statistical model and may be compared to a large library of known words, phrases, sentences, etc. The Sound recognition module 211 may then determine what a user was most likely saying based on the statistical model comparing. In an illustrative example, a person may have on a wearable (e.g., a wrist band) that includes the microphone sensor(s) 201. The microphone sensor(s) 201 may measure the decibel (dB) level of the person's voice as he/she is having a conversation. The sound recognition module 211 may also interpret what the user is saying.

The GSR sensor(s) 203 measure the Galvanic Skin Response. The Galvanic Skin Response (also known as electrodermal response) is the change in electrical properties of certain portions of a person's skin, which is caused by an interaction between environmental events and a person's psychological state. This may also referred to as a person's stressed state. When a person is in a particular heightened psychological or physiological aroused state, eccrine glands may produce sweat, which may be conductive and consequently a heighted reading may occur. To measure this response, skin conductance or resistance may be measured. In an illustrative example, a user may panic in response to some external event and experience an elevated secretion of sweat from the eccrine glands, which may cause an elevated spike in GSR. The GSR sensor(s) 203 may accordingly make the proper elevated reading.

The image capture sensor(s) 205 capture one or more still frames and/or video stream of an environment and/or objects in an environment. For example, the image capture sensor(s) 205 may be a camera or a surveillance system. The object recognition module 213 may include one or more object recognition algorithms in order to identify what that image capture sensor(s) captured. In some embodiments, the object recognition module 213 includes a feature detector, a hypothesis module, a model database, and a verification module. The feature detector detects object edges and line segments (e.g., polylines) and circular arcs. These features are combined in various ways to form the features for matching. The features detected are compared and matched against logical features in the model database to identify an object. The hypothesis module then assigns a probability or confidence measure to some or each of the objects in the module database. The verification module then selects one or more objects from the model database as candidates with the highest matching scores to the detected feature(s). For example, the object recognition module 213 may receive data from the image capture sensor(s) 205 and verify that the data corresponds to a person riding a bike.

In an illustrative example of how the object recognition module 213 (or text analyzer 215) works, a user's mobile phone may include digital photographs and/or graphical symbols (e.g., photographs, emoticons, etc.). A user may have recently sent a text message with a person that is visibly sad. An application (e.g., the application 135 of FIG. 1) may be configured to transmit (e.g., over a wireless network) the photograph to the object recognition module 213 when they are generated (or every Nth time period). The Object recognition module 213 may then use these object recognition algorithms to determine that the photograph of the face is associated with someone who is sad.

The text input 207 corresponds to one or more written characters (e.g., words, symbols, numbers, letters) that a user inputs. The text input 207 may be derived from various user resources, such as social media platforms, Short Message Service (SMS) text messages, blogs, web-journals, etc. In some of these embodiments, modules that include data scrapers are configured to extract data (e.g., from a website) and transmit web pages, posts, texts, etc. to the text analyzer 215. A data scraper (e.g., a screen scraper) extracts data from any source. For example, a data scraper may be a web scraper that uses a web crawler to automate fetching or downloading of a social media page and extract data from corresponding HTML pages. In another example, an automated module scrape SMS text messages generated by a user every Nth time period and responsively transmit the messages to the text analyzer 215.

After the data is extracted it may be transmitted to the text analyzer 215 in order to interpret the character(s). The text analyzer 215 may perform various methods and techniques for analyzing structured data, unstructured data (e.g., data from a web page via Object Character Recognition (OCR) techniques), and/or multimedia (e.g., images, audio, video, etc.). In some embodiments, the text analyzer 215 and/or behavior analysis module(s) 220 parses passages of documents and various modules are used to process the data, such as a tokenizer, a part-of-speech (POS) tagger, a semantic relationship identifier, and a syntactic relationship identifier.

A tokenizer is a computer module that performs lexical analysis. Tokenizers specifically convert a sequence of characters into a sequence of tokens. A token is a string of characters included in an electronic document and categorized as a meaningful symbol. Further, in some embodiments, a tokenizer identifies word boundaries in an electronic document and breaks any text passages within the document into their component text elements, such as words, multiword tokens, numbers, and punctuation marks. In some embodiments, a tokenizer receives a string of characters, identify the lexemes in the string, and categorize them into tokens.

A POS tagger is a computer module that marks up a word in passages to correspond to a particular part of speech. The POS tagger reads a passage or other text in natural language and assigns a part of speech to each word or other token. POS tagger determines the part of speech to which a word (or other text element) corresponds based on the definition of the word and the context of the word. The context of a word may be based on its relationship with adjacent and related words in a phrase, sentence, question, or paragraph. In some embodiments, the context of a word may be dependent on one or more previously analyzed electronic documents (e.g., the content of one source document may shed light on the meaning of text elements in another source document). Examples of parts of speech that may be assigned to words include, but are not limited to, nouns, verbs, adjectives, adverbs, and the like. Examples of other part of speech categories that a POS tagger assigns includes, but are not limited to, comparative or superlative adverbs, wh-adverbs, conjunctions, determiners, negative particles, possessive markers, prepositions, wh-pronouns, and the like. In some embodiments, POS taggers annotate tokens of a passage with part of speech categories.

A semantic relationship identifier is a computer module that identifies semantic relationships and/or domains of recognized text elements (e.g., words, phrases) in documents. In some embodiments, a semantic relationship identifier determines functional dependencies between entities and other semantic relationships. For example, when a user generates a set of terms for the text analyzer 215 to analyze (e.g., cat, dog, mouse), a semantic relationship identifier may first identify the semantic category of the terms (e.g., animal) to perform further analyses.

Consistent with various embodiments, a syntactic relationship identifier is a computer module that identifies syntactic relationships in a passage composed of tokens. Syntactic relationship identifiers determine the grammatical structure of sentences, for example, which groups of words are associated as phrases and which word is the subject or object of a verb. Syntactic relationship identifiers may conform to formal grammar.

The motion sensor(s) 209 include any sensor(s) configured to measure some aspect of motion of a user. For example, in some embodiments, the motion sensor(s) 209 include an accelerometer and/or a gyroscope. These sensors may be used for measuring an acceleration and/or an angular velocity of a person. Lack of movement, for example, may indicate that a person has fallen or in a depressed state. Conversely, rapid continuous movement may indicate that a person is nervous or anxious.

The user device(s) 211 may include various information about a user that is transmitted to the behavior analysis module 220. The user device(s) 211 may also be the output mechanism used to communicate the results generated in the behavior analysis module 220 to a user. In an illustrative example, the user device(s) 211 includes a mobile device. The mobile device may have various user information stored therein, such as user schedules, calendar events, text messages, etc. that is analyzed by the behavior analysis module 220. In some embodiments, the user device(s) 211 includes an application configured to let a user input data to be transmitted to the behavior analysis module 220, such as a favorite song, a selected music service, user medical history, medication recommendations, favorite quotes, favorite television show, etc.

According to the computing environment 200, the behavior analysis module(s) 220 receives and analyzes each of the sensor data from the various sensors and provides an associated output. In some embodiments, the behavior analysis module 220 is the behavior analysis module(s) 120 as illustrated in FIG. 1. The monitoring component 217 collects each of the data obtained from the microphone sensor(s) 201, GSR sensor(s) 203, image capture sensor(s) 205, text input 207, motion sensor(s) 209, and the user device(s) 211.

The trigger component 219 receives the data gathered at the monitoring component 217 in order to analyze the data and provide appropriate corresponding output responses. The data received at the trigger component 219 may be compared to one or more unstructured/structured data sources, policies, rules, and/or thresholds in order to determine whether the user is in one or more particular health states or experiences a particular health episode so that appropriate output response can be transmitted. For example, a dB (decibel) reading from the microphone sensor (s) 201 may read at 75 dBs for a 3 minute continuous time period. The triggering component 219 may check the dB reading against a policy dB model conditional statement, which may specify that if the dB reading is over 70 dBs, an inference of yelling can be made, indicating stress or anger. The quantity of time at the particular dB level may be weighted or scored as a more severe, since the dB level was sustained for 3 minutes. In response to the inferring of stress or anger, the trigger component 219 may transmit or cause to be outputted, a response to the user device(s) 211. For example, the trigger component 220 may cause a smart speaker to output an audio response indicating the dB level identified and a predicted health state.

In some embodiments, the trigger component 219, queries one or more data sources 225 (e.g., the information corpus 145; the remote data source(s) 135) to find remedies for anger or other health states in order to provide an appropriate output response to the user device(s) 211. For example, the trigger component 219 may query the information corpus 145. The information corpus 145 may include millions of structured and unstructured data sets. If the user experienced an anger episode as defined by a policy, the trigger component 219 may generate one or more hypotheses for communicating to the user in how to remedy or cope with the anger episode. The trigger component 219 may search for evidence to support or refute the hypothesis and score the data based on statistical modeling. For example, the trigger component 219 may identify, via NLP, that 10,000 documents, specify particular remedial actions to take when confronted with an anger episode. NLP may identify that a first remedial action (e.g., take deep breaths) is listed in 80% of the documents and no other remedial measure is mentioned as often. Accordingly, the trigger component 219 may score this first remedial action as the highest candidate for treatment of the anger and indicate as such in an output response to the user device(s) 211.

In some embodiments, the trigger component 219 searches a source (e.g., the user history data store 125 of FIG. 1) of the data sources 225 to determine one or more triggers and/or predicted behaviors associated with the behavior analysis module(s) 220. In an embodiment, the data source includes a history (e.g., time slices within the user history data store 125) of various records that include past readings from the sensors and particular activities a user was engaging in (e.g., via object recognition or conversations picked up from the microphone sensor(s) 201) in order to predict a particular behavior that has not yet occurred and/or a trigger for a particular behavior. For example, via data mining and machine learning techniques, it may be determined that every time a user experienced anger according to a policy and over a month span, he/she may have also been driving 90 percent of the time. Accordingly, if it was determined that the user was driving at a later time (e.g., before another anger episode), the trigger component 219 is configured to output a message to the user device(s) 211 indicating that the user should be on the lookout that an anger episode may arise because the user is driving. Instead of or in addition, the trigger component 219 may identify driving or experiencing road rage as the trigger for his/her anger as a result of the gathered statistics. Prediction algorithms are discussed in more detail below.

In some embodiments, predicting another health episode or trigger may in addition or instead be based on querying additional static data resources of that data sources 225. For example, the trigger component 219 may search a data store (e.g., the remote data source(s) 135) that lists common triggers of particular health states that are not specifically tied to a history of a particular user being monitored. Accordingly, output responses may be generated based on this information.

In some embodiments, the trigger component 219 analyzes a word or set of words of a user obtained from the microphone sensor(s) 201 instead of or an addition to analyzing a sound level (e.g., dB). For example, certain words or phrases may be associated with particular health states as indicated by a policy and when the user speaks those words, the sound recognition module 211 may identify the words and the trigger component 219 may generate an appropriate response. In some embodiments, the output provided by the trigger component 219 to the user device(s) 211 may be postponed or bypassed until analysis is performed by the summary component 221, which is described in more detail below.

The trigger component 219 may analyze the data received from the image capture sensor(s) 205 in various manners and provide an appropriate output. For example, the data sources 225 may include template images associated with particular health states and when the object recognition module 213 identifies an image within a threshold similarity of the template images, an appropriate output to the user device(s) 211 may be transmitted. In an example illustration, the template images may include facial images that indicate stress, sadness, and/or anger and whenever the image capture sensor(s) 205 captures an image of a user that resembles the template image states within a threshold, particular outputs may be generated at the user device(s) 211. In some embodiments, the data sources 225 may include activity or other non-facial templates instead of or in addition to facial recognition templates that indicate particular health states. In an example illustration, the templates may include: gait patterns that indicate distress or other health states, objects associated with danger, such as weapons, and/or other objects associated with a particular health state of a particular user.

The trigger component 219 may analyze the text input 207 in various manners. For example, certain social media or texting words, phrases, and/or specified activities may be associated with particular health states and a corresponding word/activity bank may be stored to at least one of the data sources 225. Accordingly, whenever a user inputs a particular word, phrase, and/or activity or otherwise indicates something associated with a particular health state, the trigger component 219 will transmit a notification to the user device(s) 211. In an example illustration, a user may have recently indicated on a social media post, "I'm giving all my belongings away, message me if you want anything." The trigger component 219 may search the data sources 225 and determine that this phrase is consistent with depression and other serious health states. Accordingly, the trigger component 219 may output a response at the user device(s) 211 for particular remedies or coping mechanisms associated with depression.

The summary component 221 obtains and analyzes historical data from at least some of the data sources 225 (e.g., the user history data store 125) and provides an appropriate output at the user device(s) 211. In some embodiments, after the trigger component 219 analyzes the sensor data at a particular time slice (e.g., 4 P.M.) and/or a series of time slices (e.g., 4 P.M to 9 P.M.), the trigger component stores the sensor data corresponding to the time slice and/or series of time slices to one of the data sources 225. The summary component 221 then retrieves the time slice and/or series of time slices for an output response. The summary component 221 may analyze a series of time slices and outputs a response to the user device(s) 211 based on any time slice sequence. For example, the summary component 221 may analyze any particular data that was sampled for an hour, day, week, and/or month and provide an appropriate output. In an example illustration, the summary component 221 may communicate with an API backend server requesting a day's summary of a particular person's obsessive compulsive behavioral health state. The API may then communicate with a historical database (e.g., as found with a data source of the data sources 225) to obtain the data. The backend server may then identify various factors that the user did in a single day. For example, the user may have: washed hands 20 times that day (e.g., as identified from the image capture sensor(s) 205), locked the front door 8 time (e.g., as identified by the image capture sensor(s) 205), repeated a question 15 times (e.g., as determined by the microphone sensor(s) 201), and has not cleaned his/her shoes in ten days (indicating an improvement of not engaging in a particular behavior).

In some embodiments, the summary component 221 provides a behavioral health index (BHI) to the user device(s) 211 and shows variations in the index against time. A BHI is an indicator of psycho social physiological well-being. In embodiments, a BHI module consolidates each of the behavior plugin data and provides an overall health index based on all of the data. For example, a first behavior plugin (e.g., behavior plugin 131) is associated with assessing OCD; a second behavior plugin (e.g., behavior plugin 133) is associated with assessing anger; a third behavior plugin may be associated with assessing depression. The BHI may analyze each of the OCD, anger, and depression readings to find correlations between the data and output a final health index to the user.

The output to the user device(s) 211 may be any suitable output according to any suitable automated or user-specified output. For example, the output may be an auditory output to a speaker, written indicia to a display screen of a computing device, and/or an activation of a device in order to help cope with or remedy the particular health state. In an illustrative example of an activation of a device, in response to the behavior analysis module(s) 220 determining that a user is experiencing an anxiety or depression episode, the trigger component 219 and/or the summary component 221 may communicate, over a wireless network, to an API associated with a music service and instruct the service to play a particular song on a smart speaker to reduce the anxiety or depression. In another illustrative example, in response to the behavior analysis module(s) 220 determining that the user is experiencing depression, the behavior analysis module(s) 220 may communicate and instruct, over a network, a smart treadmill to be activated. The treadmill may be activated because some research suggests that exercise releases endorphins, which are natural chemicals that are produced in the body to help with mood among other matters.

In yet another illustrative example, in response to the behavior analysis module(s) 220 determining that the user is experience or will experience an obsessive compulsive episode, the behavior analysis module(s) 200 may communicate and instruct, over a network, a smart locking system to lock a door and/or a smart cleaning bot (e.g., a ROBO-VAC) to start cleaning in order to prevent the user to perform repetitive actions associated with locking doors and/or cleanliness. Multiple other devices can be activated in response to determining particular health states such as a television, lights, thermostat, switch device (e.g., BELKIN'S WeMO SWITCH), a mobile device (e.g., instructing the mobile device to input a phone number so that a particular person is contacted), and/or a transceiver located on a prescription container (e.g., to instruct the user to take his/her medication).

Figure 3:
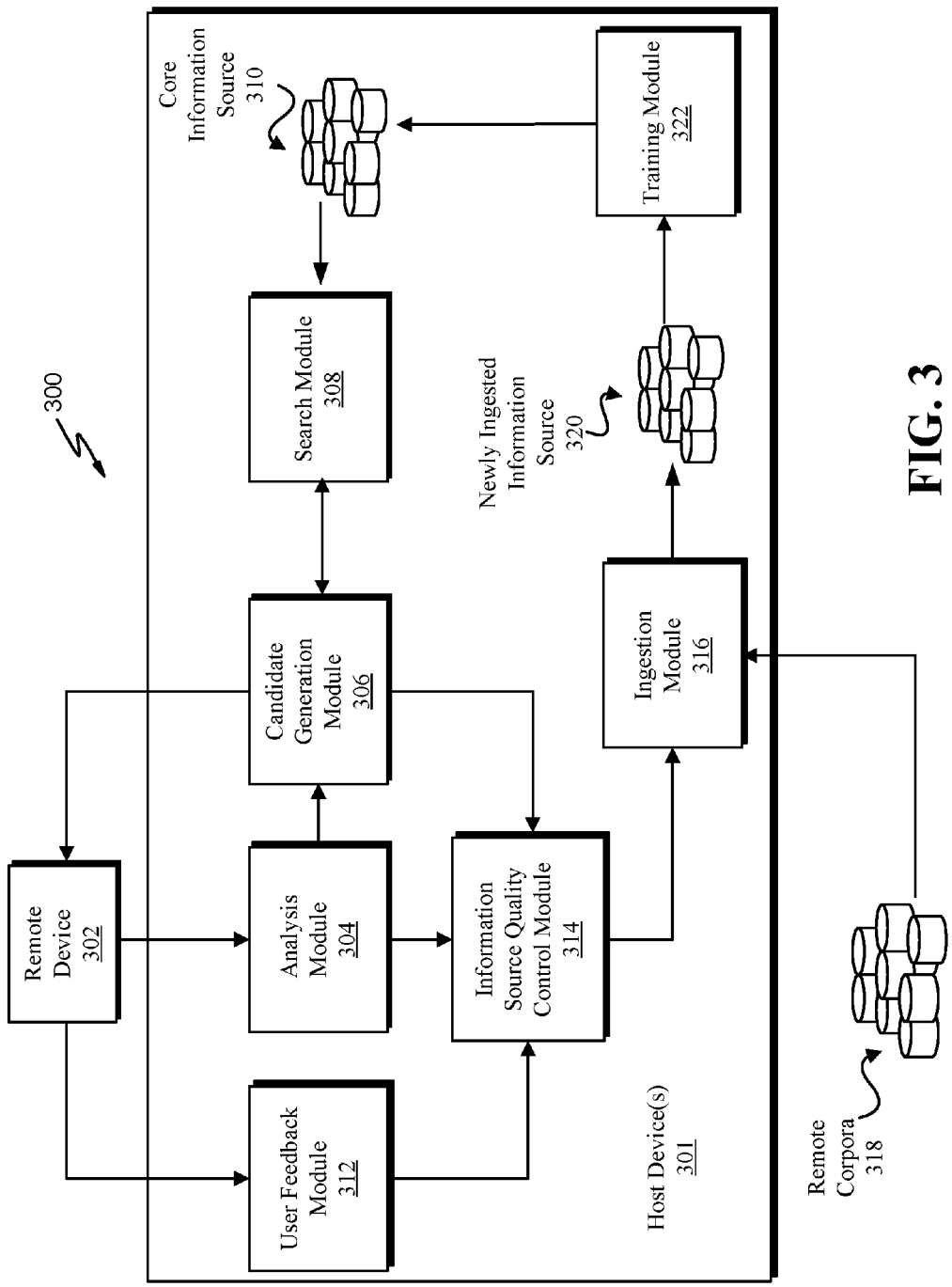
FIG. 3 illustrates a block diagram of an example high level logical architecture of a personal assistant computing system, according to embodiments.

FIG. 3 illustrates a block diagram of an example high level logical architecture of a personal assistant computing system, consistent with embodiments. In some embodiments, host device(s) 301 and remote device 302 may be embodied by server(s) 114 and user device(s) of FIG. 1 (and/or the sensor device(s) 103), respectively. In some embodiments, the analysis module 304, located on host device 301, may receive an input (e.g., a voice command and/or sensor data) from a remote device 302, and can analyze the input to produce information about the input (e.g., provide an answer to a question and/or provide behavioral remedies for a health state once detected). This may be accomplished, for example, by using the behavioral analysis module(s) 220 and the data source(s) 225 of FIG. 2. The information produced by analysis module 304 may include, for example, what queries need to be formulated based on a health state detected.

Next, the candidate generation module 306 may formulate queries from the output of the analysis module 304 and then pass these queries on to search module 308 which may consult various resources (e.g., resources within the information corpus 145, such as social media portals, blogs, books, scientific studies, user history data stores, newspapers, etc.) to retrieve documents that are relevant for providing an output (e.g., the output to the user device(s) 211 according to FIG. 2). As used herein, documents may refer to various types of written, printed, or electronic media (including passages, web-pages, database files, multimedia, etc.) that provide information or evidence. As illustrated in FIG. 3, the search module 308 may consult core information source 310. In some embodiments, the core information source is identical to the information corpus 145 of FIG. 1. As used herein, a core information source may refer to any document or group of documents that is used by a relevant personal assistant computing system to generate an appropriate output or generate candidate answers to user questions. The candidate generation module 306 may extract, from the search results obtained by search module 308, candidate answers, candidate resources (e.g., a list of coping methods and/or remedies for a particular health state), and/or other candidate outputs (e.g., listing what possible devices to activate, such as music service, smart lights, vacuum, etc.), which it may then score (e.g., with confidence scores) and rank. A final list of highly ranked candidate(s), based on a comparison of various confidence scores associated with the other candidates, may then be sent from the candidate generation module 306 to remote device 302 for presentation to the user. In addition, this information about the highly ranked candidate(s) and confidence scores may also be sent to information source quality control module 314. A user may respond, via remote device 302, to generate its own list of candidate(s) (e.g., a particular user's doctor may input tailored remedies for a health state that is specific to the user) through user feedback module 312. The user feedback module 312 may then provide this feedback to the information source quality control module 314.

In some embodiments, the information source quality control module 314 may compile and analyze information that it receives during the course of normal operations of cognitive computing system 300. This received information (e.g., information from analysis module 304, candidate generation module 306, and user feedback module 312) may be usable by the information source quality control module 314 to determine whether one or more new information sources should be ingested. When the information source quality control module 314 determines that a new information source having certain characteristics is needed (e.g., because the user feedback module 312 received user feedback that more sources should be queried), it may instruct an ingestion module 316 accordingly. Based on these instructions, ingestion module 316 may search one or more remote sources, such as remote corpora 318 (e.g., the remote data source(s) 135 of FIG. 1), in an attempt to locate one or more suitable new information sources. In some embodiments, once discovered, these new information sources may be ingested by ingestion module 316 and become newly ingested information source 320. This information source may in turn be analyzed by training module 322. This training analysis may take the form of training the personal assistant computing system to utilize more sources for providing additional potential outputs using the newly ingested information source 320 and then reviewing the quality of the output candidates. In some embodiments, once a threshold level of confidence in the new information source is met, it may be combined with core information source 310 and used to generate output candidate(s).

The various components and modules of the exemplary high level logical architecture for a personal assistant computing system described above may be used to implement various aspects of the present disclosure. For example, the analysis module 304 may, in some embodiments, be used to receive a set of sensor data indicating various health attributes of a user. The candidate generation module 306 and search module 308 may together, in some embodiments, be used to perform searches of core information source 310, identify that the user is in a particular health state, generate remedial measures (e.g., provide a user with a list of remedies for the health state), calculate confidence scores associated with the sensor data, and/or provide a corresponding output to one or more users. Further, the information source quality control module 314 may, in some embodiments, be used to analyze confidence scores and determine whether the confidence scores fail to meet one or more confidence criteria. Further, ingestion module 316 may, in some embodiments, be used to ingest new information sources (in response to an indication from the information source quality control module 314 that a confidence criteria has not been satisfied).

Figure 4:
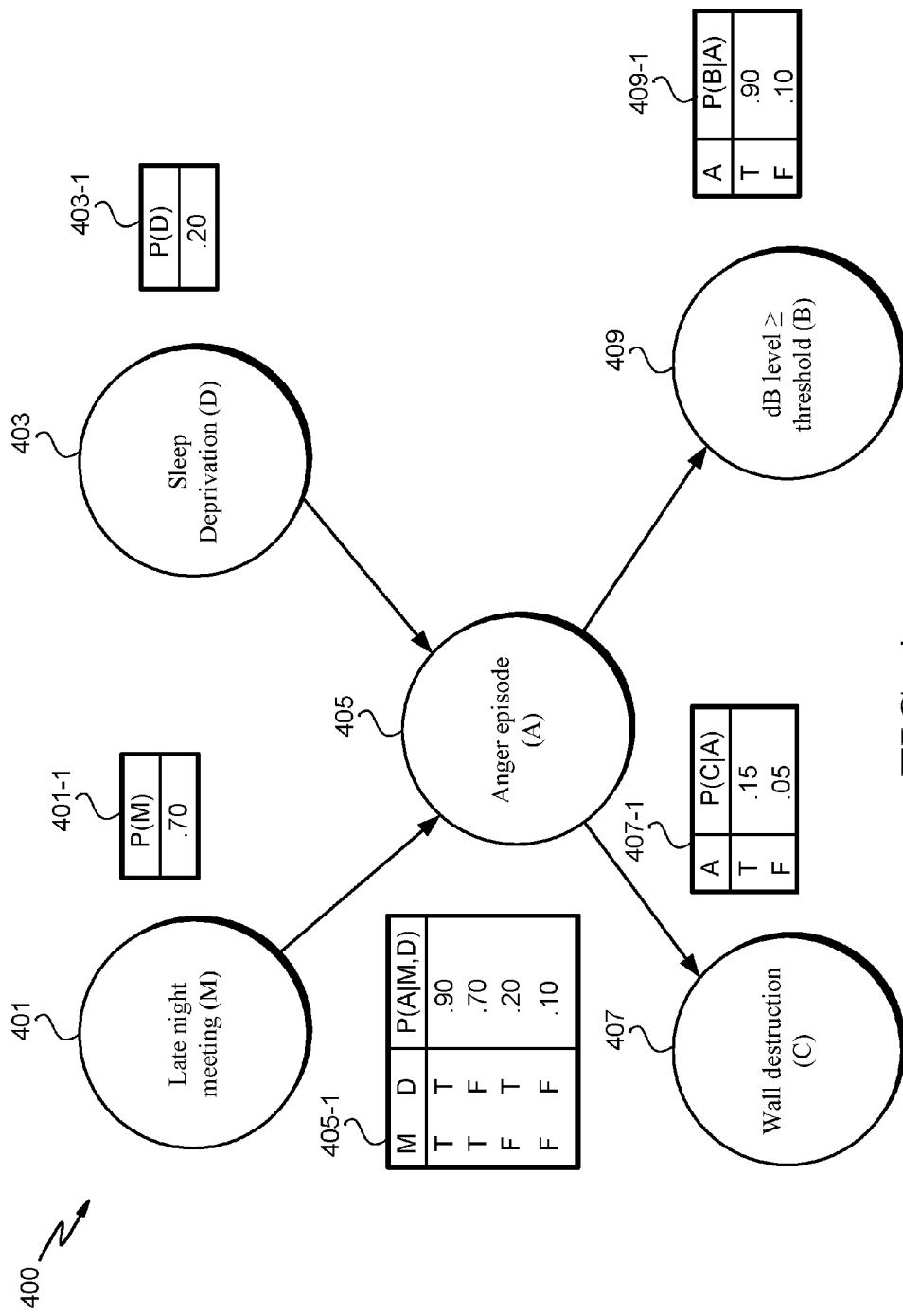
FIG. 4 is a diagram illustrating a way to predict one or more triggers, health states, and/or the effects of health states, according to embodiments.

FIG. 4 is a diagram illustrating a way to predict one or more triggers, health states, and/or the effects of health states, according to embodiments. FIG. 4 includes the Bayesian network 400, which includes the nodes 401, 403, 405, 407, arcs, and conditional probability tables 401-1, 403-1, 407-1, and 409-1. Bayesian networks are statistical mechanisms that utilize directed acyclic graphs to help predict or determine what might be a cause or association of some phenomena. Given a particular set of evidence, various statistical inferences can be made. Each of the nodes in a Bayesian network is only conditionally dependent on its immediate parents and not its non-descendants. It is understood that the Bayesian network 400 is illustrative only. Accordingly, different statistical inferences and/or nodes may be added or taken away from the network 400. For example, for the evidence of anger episode (A) corresponding to node 405, there may be multiple other parent nodes other than node 401 and 403. Likewise, there may be various child nodes, other than node 407 and 409. Further, different health states may be analyzed instead of or in addition to an anger episode, such as obsessive compulsive disorder, diabetes, depression, heart disease, chronic injury, etc.

Because the Bayesian network 400 is an acyclic directed graph, it can be stated that $$P(y1, \ldots, yn) = \Pi_{i=1}^{n} P(yi | \text{Parents}(Yi))$$    Equation #1

Where Parents(Yi) denotes immediate predecessors of Yi in the graph 400. Accordingly, the joint distribution of individual child variables P (y1, ..., yn) (i.e., the probability that the child variables will occur) is equal to the production or probability of each individual child variables (e.g., anger episode (A)) will occur with individual values given the parents variables (e.g., sleep deprivation (D)) of that child variable and the child variables' values.

The eventual output may include the individual conditional probability tables of the Bayesian network 400. The network 400 illustrates that there is one evidence variable Anger episode (A) corresponding to node 405. The joint probability table 401-1 indicates that if a late night meeting (M) occurs (node 401) (e.g., as indicated by a calendaring indicia), there is a 70% chance that the anger episode (A) (node 405) will occur. Likewise, the conditional probability table 403-1 indicates that if sleep deprivation (D) occurs (node 403) (e.g., as sensed via object recognition), there is only a 20% chance that the anger episode (A) will occur. These observations may be made via machine learning and/or other prediction techniques (e.g., via other parent nodes of nodes 401 and/or 403). Machine learning predicts a set of outcomes without specifically requiring user programming. Thus machine learning builds algorithms based on receiving input data. Accordingly, these specific inference values within the conditional probability tables may be based a history of observations (e.g., via the sensors of FIG. 2) and making associations of the variables through statistical inference. For example, making the observation that if a user had a late night meeting, he/she is 70% likely to become angry may be based on making 100 observations of the user becoming angry. Out of the 100 episodes, 70 of the episodes may have been preceded by a late night meeting (e.g., as defined by any meeting after 8 P.M.), thereby suggesting that a trigger or cause of the anger episode is very likely a late night meeting. Once the system learns of this statistically significant likelihood, it may offer specific warnings, alerts, messages, or other actions to the user (e.g., turn on a particular device) indicating that an anger episode (or other health state) is very likely to occur, given that the user had a late night meeting last night.

The conditional probability table 405-1 gives the singular and joint probability that an anger episode will arise depending on the truth values of the variables from node 401 and 403. That is, the probability of anger episode (A) given late night meeting (M) and sleep deprivation (D). Specifically, it indicates that late night meeting (M) and sleep deprivation (D) are true (i.e., they were detected), then there is a 90% chance that an anger episode will arise. Likewise, if M is true but D is false, then there is a 70% chance that A will occur. Further, if M is false but D is true, there is only a 20% chance that A will occur. Finally, if both M and D are false, there is only a 10% chance that A will occur.

The conditional probability table 407-1 indicates the probability that wall destruction (C) will occur, given that anger episode (A) occurred. For example, when some people become angry they may become aggressive and punch holes through walls or perform other physical aggressive acts. The table 401-1 indicates that if A is true, then there is only a 15% chance that wall destruction will occur. And even if A is not true (no anger is involved), then there is only a 5% chance that wall destruction will occur. Given this information, the prediction system may selectively choose not to provide outputs (e.g., remedies, coping mechanisms for physical aggression) corresponding to the node 407 given that there is a relatively low change that the user will engage in this activity.

Conversely, the conditional probability table 409-1 indicates the probability that a dB level will be greater than or equal to a threshold (B) given that A occurred. For example, instead of or addition to a user becoming physically aggressive by destroying a wall consistent with node 407, he/she may only elevate his/her voice at a shouting level above a dB level. The table 409-1 indicates that if A is true, there is a 90% probability that B will occur (e.g., the user will shout). Conversely, if A is false, there is only a 10% probability that the dB level will be greater than or equal to a threshold. This may indicate a strong inference that if an anger episode arises, there is high statistically significant chance that shouting will ensue. Accordingly, outputs (e.g., the outputs to the user device 211 as specified in FIG. 2) may be tailored to the high chance of shouting (e.g., strategies for refraining from shouting may be transmitted to the user).

Inferences can be made based on the calculations of any one of these nodes. Further, any one of the nodes in FIG. 4 may be predicted regardless of the direction of prediction.

For example, a probability of sleep deprivation (D) (node 403) may be calculated given the dB threshold level at node 409. That is:

$$P(D | B = t) = \frac{P(B = t | D) * P(D)}{P(D)} = \alpha P(B = t, D) \quad \text{Equation \#2}$$

Where $$\alpha = \frac{1}{P(B)}$$

Therefore, the probability that D will occur given that B is true (i.e., decibel level is above the threshold) is equal to the probability that B is true given that D occurs multiplied the probability that D occurs. This is divided by the probability that D occurs. This is equal to alpha, the normalizing constant, multiplied by the probability that B is true and D.

Figure 5:
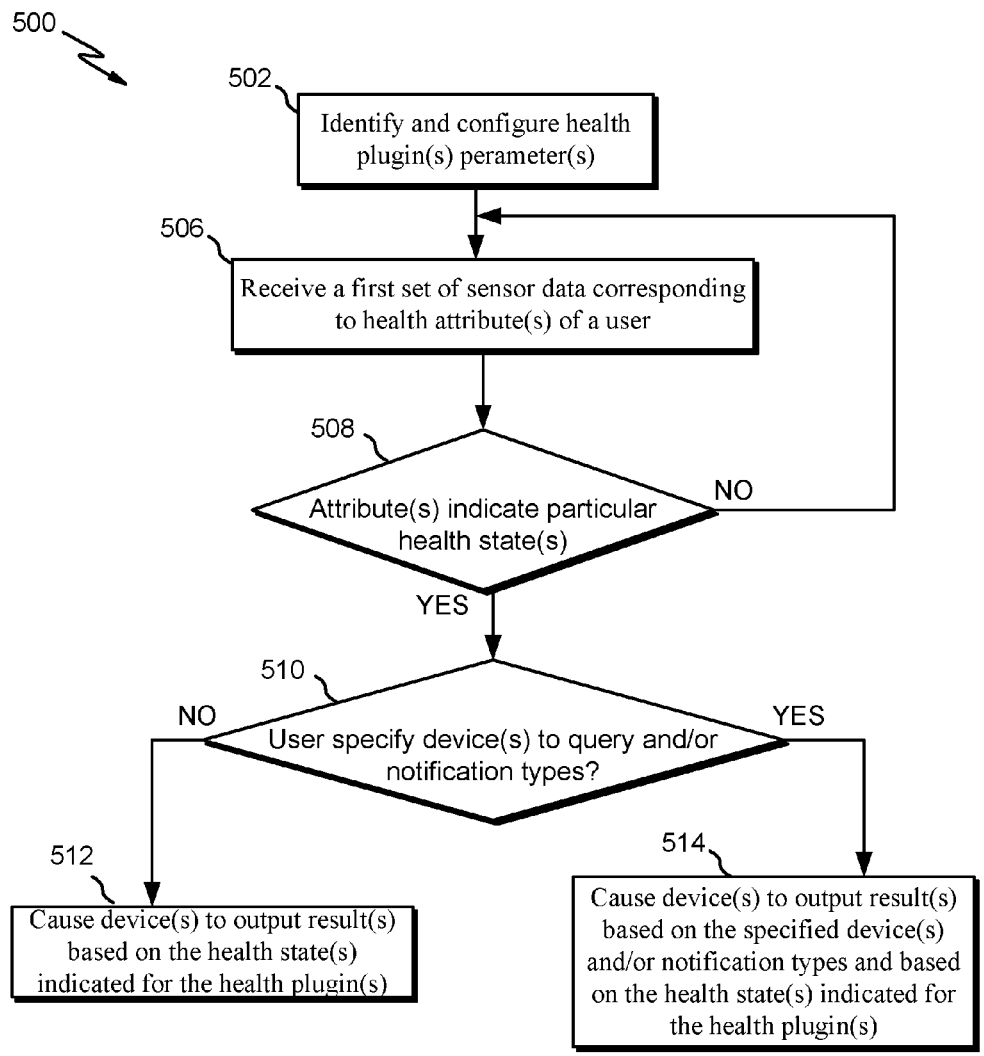
FIG. 5 is a flow diagram of an example process for causing a device to output a result based on one or more health states indicated for one or more particular health plugins, according to embodiments.

FIG. 5 is a flow diagram of an example process 500 for causing a device to output a result based on one or more health states indicated for one or more particular behavior plugins. The process 500 (as well as any other processes disclosed herein, e.g., 600, 700, 800, 900) may be performed by processing logic that comprises hardware (e.g., circuitry, dedicated logic, programmable logic, microcode, etc.), software (e.g., instructions run on a processor to perform hardware simulation), firmware, or a combination thereof.

The process 500 may begin at block 502 when health plugin (e.g., behavior plugin 131) parameter(s) are identified and configured. These parameter(s) may be identified based on a particular application that a user has downloaded or accessed. For example, the user may download the application 135 of FIG. 1. The user may then register and configure the health plugin(s) by registering various services and/or devices specific to the health plugin(s). For example, within a graphical user interface of an application, the user may define a particular music service, physician service associated with his current physician, and/or device(s) to use for sensor input gathering/output (e.g., smart surveillance device, smart light system, etc.) and/or notification specification. The application may then connect, over a wireless network(s), to a server(s) (e.g., the server(s) 114 of FIG. 1) in order to inform the server(s) which additional server(s) to communicate with, device(s) to use for sensor sampling, and/or devices to notify for an output response. In some embodiments, the health plugin parameters include patient history.

Per block 506, a first set of sensor data may be received (e.g., over one or more networks by the behavior analysis module 120 of FIG. 1), which corresponds to one or more health attributes (e.g., behavioral health, such as depression) of a user. For example, a surveillance system, an accelerometer data, and/or a microphone may measure some health attribute of a user (e.g., data representing a heart rate, movement rate, words of a user, etc.). Some or each of these sensors may include an analog-to-digital converter in order to transmit sensor data over a network to one or more servers for the receiving at block 506.

Per block 508, it may be determined (e.g., via the behavior analysis module 120 of FIG. 1) whether the one or more health attributes indicate one or more particular health states based on analyzing the sensor data. For example, the sensor data may indicate that the user is in an anger state, depressed state, anxious state, stressed state, and/or any other emotional or mental state. In some embodiments, the determining at block 508 occurs via a processor-based inference technique. For example, a processor-based inference technique may include generating a hypothesis based on the sensor data and search the information corpus 125 of FIG. 1 in order to support or refute the hypothesis. Based on the sensor data received, each document or passage within the information corpus 125 may be scored based on statistical modeling called weighted evidence scores. The evidence scores may indicate that there is a high likelihood that the user is experiencing a particular health state given the sensor data. In some embodiments, the processor-based inference technique may in addition or instead include other predictive analytics and data mining algorithms (e.g., Bayesian inference algorithms). In some embodiments, the processor-based inference technique may instead or in addition include making inferences based one whether the one or more attributes meet a policy threshold (e.g., pre-defined rules that indicate whether someone is stressed—e.g., particular GSR and pulse oximeter readings). If the one or more health attributes do not indicate particular health states, attribute(s) of the user may continue to be sampled via the sensors and other sensor data may continue to be received per block 506. Accordingly, various user attributes be measured in real-time or near real time in order to provide immediate outputs if needed due to a sudden change in one or more health states.

Per block 510, if the attribute(s) do indicate particular health state(s), then it may be determined whether the user specified one or more devices to query and/or notification types. For example, at the identification and configuration of health plugin(s) at block 502, the user may have indicated that she wants to be notified a particular quantity of times every day regarding her health status and that every time a health state is indicated or identified given the attributes, a particular device should be activated (e.g., a television for playing a particular movie, a thermostat to set to a particular setting, etc.). Notification types may include what device(s) the user wants to be notified on, whether the user wants a summary report of her health at the end of the day (or any other time period), whether the user wants to be notified every time one or more health states are indicated or identified, etc. In some embodiments, the system may be configured to receive or change notification types/specific devices to query in real-time or near real-time instead or in addition to setting this information at block 502.

Per block 514, if the user did specify one or more devices to query and/or notification types and such information is identified, a module (e.g., the behavior analysis module 120) causes one or more devices to output one or more results based on the specified device(s) and/or notification types. The result(s) may be outputted also based one the health state(s) indicated for the health plugin(s). Per block 512, if the user did not specify one or more devices to query and/or notification types, then via a default or learned setting (e.g., via machine learning), a module may cause one or more devices to output one or more results (e.g., cause a smart speaker to output the particular health state(s) indicated and associated remedies/coping mechanisms) based on the health state(s) indicated for the health plugin(s).

Figure 6:
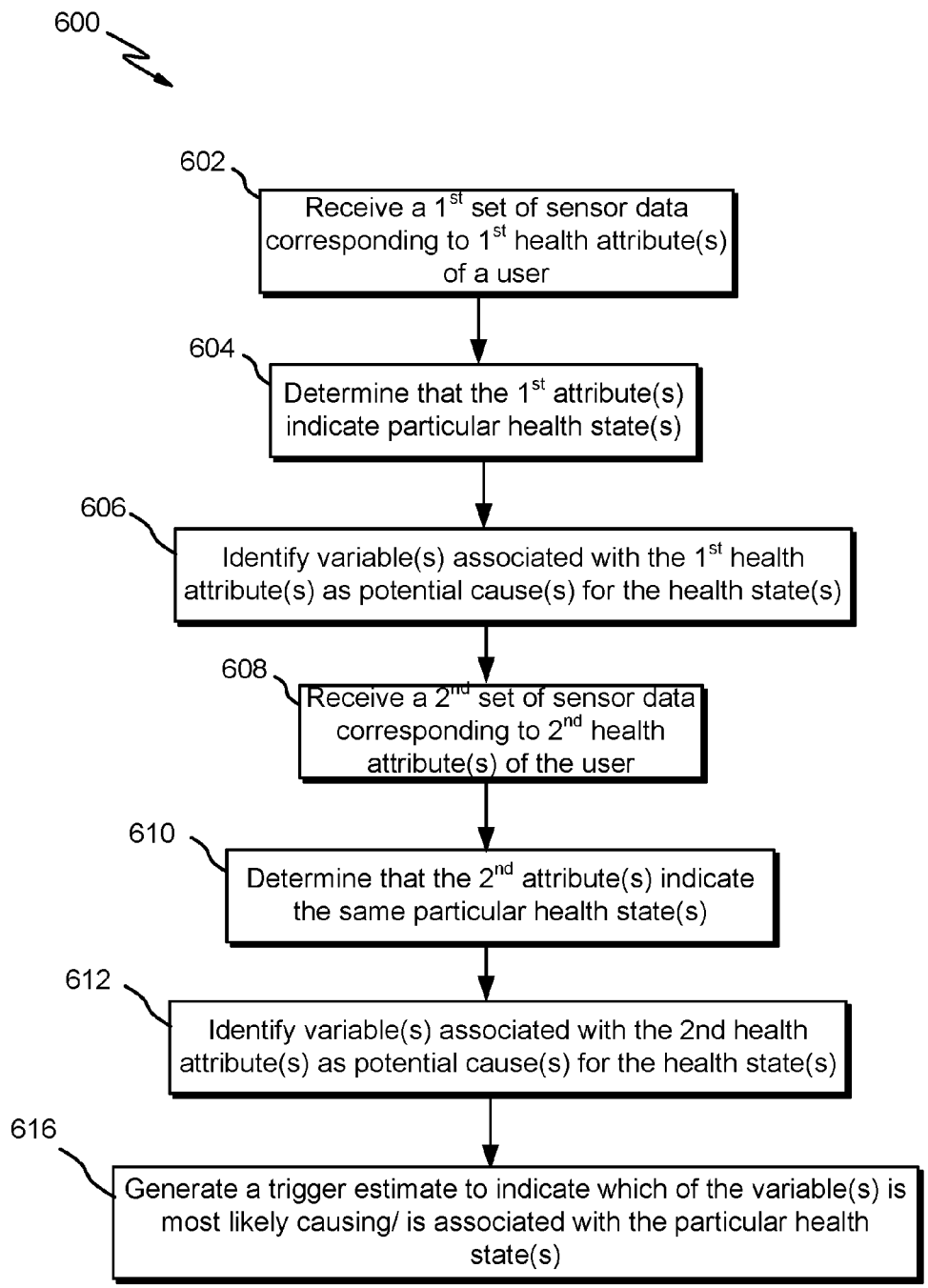
FIG. 6 is a flow diagram of an example process for generating a trigger estimate, according to embodiments.

FIG. 6 is a flow diagram of an example process 600 for generating a trigger estimate, according to embodiments. The generating of the trigger estimate may occur via one or more predictive technology methods (e.g., via the Bayesian inferences as specified in FIG. 4). The generating of the trigger estimate includes identifying one or more variables as at least one potential and/or likely cause for why a user is in a particular health state.

At block 602, a first set of sensor data may be received, which corresponds to a first set of health attribute(s) of a user. Per block 604, it may be determined that the first set of attribute(s) indicate one or more particular health states. Per block 606, one or more variables associated with the first set of health attribute(s) are identified as potential cause(s) for the health state(s). For example, referring back to FIG. 4, the variable "Late night meeting (M)"/node 401 may be identified as a potential cause for anger episode (A)/node 405. The variables may be identified as potential causes in any suitable manner. For example, every activity sensed (e.g., user actions via the image capture sensor(s) 205 of FIG. 2) within a threshold time period (e.g., 2 days) of when the particular health(s) states are identified may be identified as variables associated with the particular health state(s).

Per block 608, a second set of sensor data may be received, which corresponds to second attribute(s) of a user. The first set of sensor data received at block 602 may correspond to a first time period that sensor data was received and the second set of sensor data received at block 608 may correspond to a second subsequent time period that sensor data was received. Per block 610, it may be determined that the second attribute(s) indicate the same particular health state(s). For example, at the first time at block 602, it may be determined that the sensor data indicated a first hypoglycemic episode. At the second time, it may be determined that the sensor data also indicated another hypoglycemic episode.

Per block 612, one or more second variables may be identified, which is associated with the second health attribute(s) as potential cause(s) for the health state(s). For example, referring back to FIG. 4, in addition to identifying late night meeting (M) as a variable, sleep deprivation (D)/node 403 may also be identified as a variable as a potential cause for the anger episode (A). In another example, the same variable (e.g., sleep deprivation (D)) may be identified twice or multiple times as a variable each time the health state(s) are indicated or identified.

Per block 616, a trigger estimate may be generated (e.g., by the behavior analysis module(s) 120) to indicate which of the variables identified at blocks 606 and 612 is most likely causing or associated with the particular health state(s) indicated. The trigger estimate may include scoring a first variable higher than a second variable, which indicates that the first variable has a higher likelihood of being a cause for why the user is in one or more health states when compared to the second variable. For example, referring back to FIG. 4, the conditional probability tables score the late night meeting (M) variable higher than the sleep deprivation (D) variable by inferring that there is 70% chance that if the user has a late night meeting, he/she will experience an anger episode. However, if the user experiences sleep deprivation, the user only has a 20% chance of an anger episode. Therefore, the trigger estimate includes determining that the late night meeting variable is most heavily associated with an anger episode.

The generating of the trigger estimate may be useful for several purposes. For example, if the variables are associated with particular user actions, each time a user engages in a particular action that is most likely to cause a particular health state, the user may be warned of a potential ensuing health episode. In an illustrative example, subsequent to the generating of the trigger estimate at block 616, at a second time an action identical to an action variable most likely associated with a health state may be detected (e.g., the user has an 8 P.M. meeting tomorrow). In response to the detecting this variable, a module may cause a device to output a result for the user. The result may warn the user that a particular health state(s) will likely occur given the observed action variable. For example, if the user input on her calendar that a late night meeting was happening in 3 days, this information may be fed or transmitted over a network to a module (e.g., the behavior analysis module(s) 120) and the module may cause the user's device, such as a smart speaker, to warn the user before the meeting occurs that the user is very likely to experience an anger episode. The result may include remedies or other actions to do before the meeting starts so that the action variable will not be as stressful or problematic.

Figure 7:
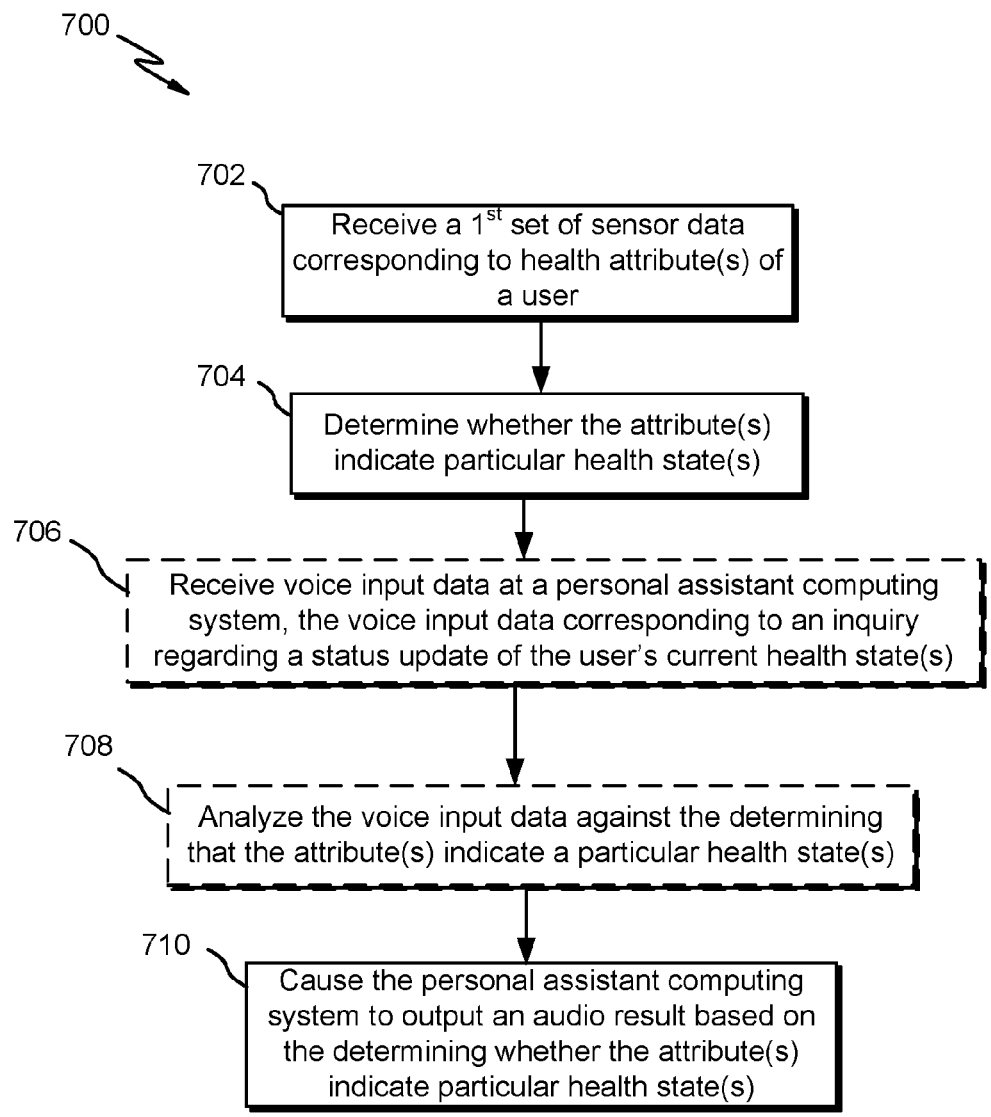
FIG. 7 is an example process for causing a personal assistant computing system to output an audio result based on analyzing sensor data, according to embodiments.

FIG. 7 is an example process 700 for causing a personal assistant computing system to output an audio result based on analyzing sensor data. Per block 702, a first set of sensor data is received, which corresponds to one or more health attributes of a user. Per block 704, it is determined whether the one or more attributes indicate one or more particular health states or episodes.

Per block 706, in some embodiments, voice input data is received from a personal assistant computing system (e.g., a smart speaker). The voice input data may correspond to an inquiry regarding a status update of a user's one or more current health states. For example, after receiving various sensor data concerning health state(s) of a user, the user may speak into a smart speaker and say "smart speaker (or other activation prompt) . . . tell me how my anger behavior and depression have been for the last week". In another example, the user may tell the smart speaker "smart speaker . . . notify me every time I have an anger episode". In some embodiments, user inputs or activation prompts to activate a smart speaker are not required. For example, sensor data can be analyzed in the background (e.g., analyzing user's words) and the user can be using the smart speaker for various unrelated purposes (e.g., to answer questions, activate lights, etc.) and the process 700 can go from block 704 to 710 (without blocks 706 or 708) in order to alert the user that a health episode/state has been detected via the personal assistant computing system. In some embodiments, a user can activate one or more sensors via a smart speaker. For example, the user can say "smart speaker . . . monitor my conversations for the next 24 hours." The system may then responsively perform blocks 702 and 704 respectively and the microphone on the smart speaker may monitor every word the user speaks.

Per block 708, in some embodiments and subsequent to block 706, the personal assistant computing system analyzes the voice input data received at block 706 against the determination at block 704 of whether the health attribute(s) indicated one or more particular health states. For example, if it was detected at block 704 that the user experienced that the user experienced a depression episodes 5 minutes ago, in response to the user input, the depression episode data is identified an prepared for generating an audio output result at block 710.

Per block 710, a module may cause the personal assistant computing system to output an audio result based on the determining whether the health attribute(s) indicated particular health state(s) at block 704. For example, using the illustration above, the module may cause a smart speaker to provide an audio output in the English language this particular phrase "you just exhibited signs of depression. Within the next 24 hours, you should exercise".

Figure 8:
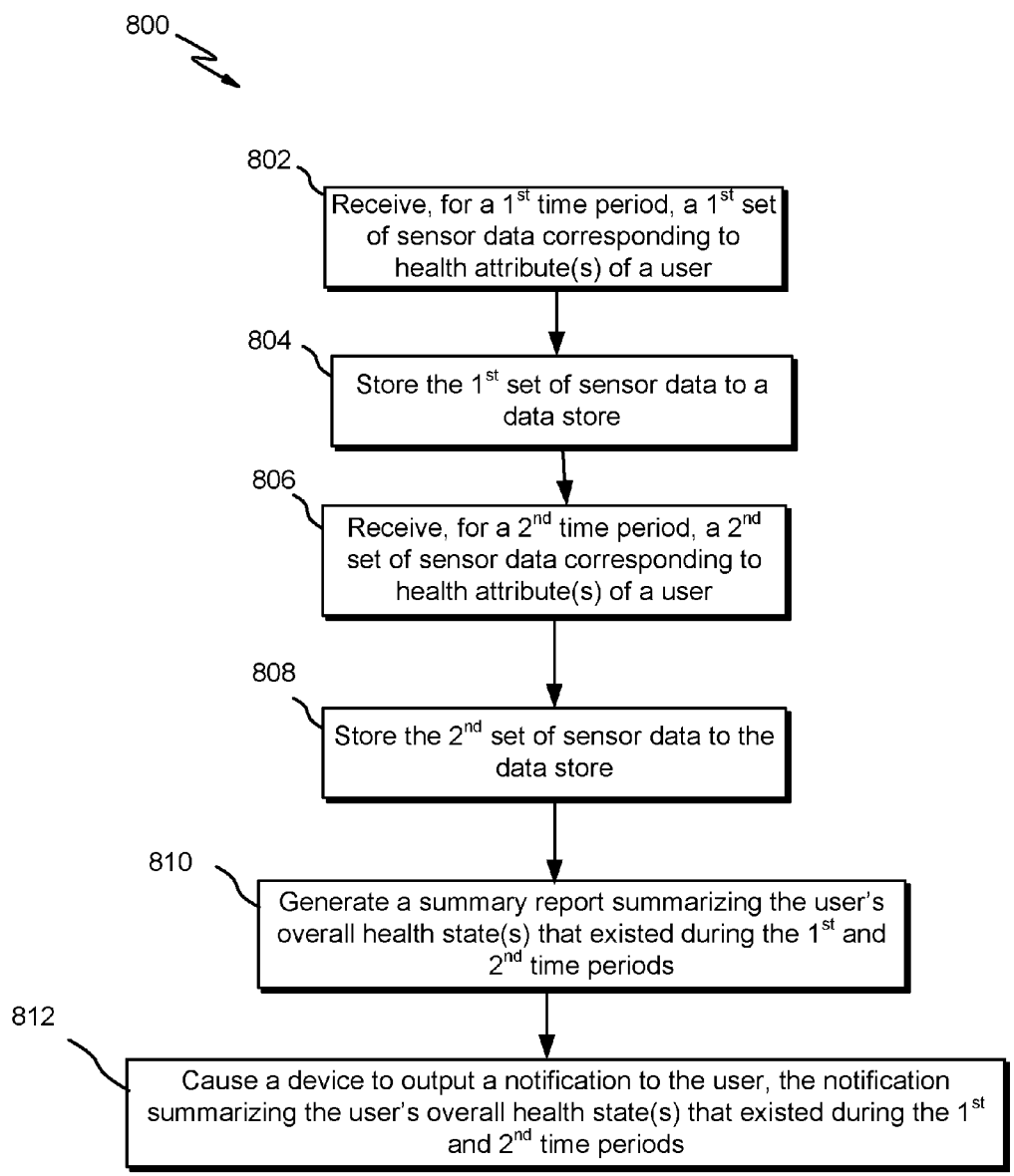
FIG. 8 is a flow diagram of an example process for generating a summary report summarizing a user's overall health state(s) that existed during a particular time period, according to embodiments.

FIG. 8 is a flow diagram of an example process 800 for generating a summary report summarizing a user's overall health state(s) that existed during a particular time period, according to embodiments. At block 802, a first set of sensor data for a first time period (e.g., a first day) is received. Accordingly, one or more sensors may sample or measure data for a particular time slice (e.g., 20 minutes). The sensor data corresponds to one or more health attributes of a user. Per block 804, the first set of sensor data is stored to a data store (e.g., the user history data store 125 of FIG. 1).

Per block 806, a second set of sensor data for a second time period (e.g., a second day) is received. The second set of sensor data also corresponds to one or more health attributes of a user. Per block 808, the second set of sensor data is stored to the data store. Per block 810, a summary report is generated (e.g., by the summary component 221 of FIG. 2), which summarizes the user's overall health state(s) that existed during the first and second time periods. For example, the first time period may correspond to a first month and the second time period may correspond to a second month. A module, such as the summary component 221, may indicate how many total times during the first and second time month a particular health episode occurred. In some embodiments, the module compares the two time periods so the user can assess any improvements or declines associated with particular health episodes. In some embodiments, the module gives a summary report on the probable triggers via a trigger estimate to indicate the likely cause(s) of the health episode(s). In some embodiments, the summary report includes a BHI, which gives a report of each health state (e.g., Anger, post-traumatic stress disorder, anxiety) that has been defined by a health plugin for the entire duration of the first and second time periods.

Per block 812, one or more computing devices (e.g., the server(s) 114 of FIG. 1) cause a device (e.g., the user device(s) 105) of FIG. 1) to output a notification to the user. The notification summarizes the user's overall health state(s) that existed during the first and second time periods. For example, the server(s) 114 may transmit a message to a smart speaker of the user, which causes the smart speaker to output an audio response detailing the summary report generated at block 810.

Figure 9:
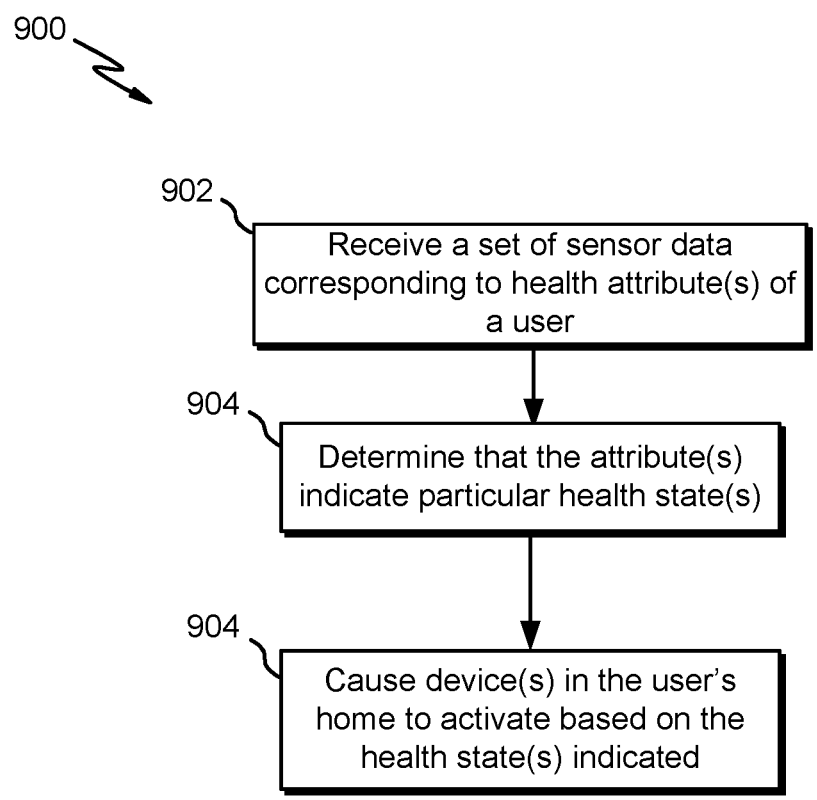
FIG. 9 is a flow diagram of an example process for causing one or more devices in a user's home to activate based on one or more health states indicated, according to embodiments.

FIG. 9 is a flow diagram of an example process 900 for causing one or more devices in a user's home to activate based on one or more health states indicated. At block 902, a set of sensor data corresponding to health attribute(s) of a user is received. Per block 904, it is determined that the attribute(s) indicate particular health state(s) or episodes (e.g., an anxiety episode has occurred). Per block 904, one or more computing devices (e.g., the server(s) 114 of FIG. 1) causes one or more devices in the user's home (or other environment) to activate based on the particular health state(s) that are indicated. For example, in response to an anger episode being detected, the server(s) 114 may communicate, over a network, with a music service server to cause a particular soothing song to play on a smart speaker of the user in order to alleviate the anger. In various embodiments, the user's environment corresponds to his/her: work environment, recreational environment, vehicle environment, and/or any other suitable environment.

FIG. 10 is a block diagram of a computing device 12, according to embodiments. As shown in FIG. 10, the computing device 12 is shown in the form of a general-purpose computing device, which is not to be construed necessarily by one of ordinary skill in the art as a generic computer that performs generic functions. Rather, the computing device 12 is illustrative only of what components a computing device may include. The components of computing device 12 may include, but are not limited to, one or more processors or processing units 16, a system memory 28, and a bus 18 that couples various system components including system memory 28 to processor 16. In some embodiments, the computing device 12 represents the user device(s) 105 of FIG. 1, the server(s) 114 of FIG. 1, and/or the sensor device(s) 103 of FIG. 1.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computing device 12 typically includes a variety of computer system readable media. Such media may be any available media that is accessible by computing device 12, and it includes both volatile and non-volatile media, removable and non-removable media.

System memory 28 can include computer system readable media in the form of volatile memory, such as random access memory (RAM) 30 and/or cache memory 32. Computing device 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein. For example, the program modules 42 may be or include the behavior analysis module(s) 120, the application 135, and/or perform any of the portion of the processes 500, 600, 700, 800, and/or 900.

Computing device 12 may also communicate with one or more external devices 14 such as a keyboard, a pointing device, a display 24, etc.; one or more devices that enable a user to interact with computing device 12; and/or any devices (e.g., network card, modem, etc.) that enable computing device 12 to communicate with one or more other computing devices. Such communication can occur via Input/Output (I/O) interfaces 22. Still yet, computing device 12 can communicate with one or more networks such as a local area network (LAN), a general wide area network (WAN), and/or a public network (e.g., the Internet) via network adapter 20. As depicted, network adapter 20 communicates with the other components of computing device 12 via bus 18. It should be understood that although not shown, other hardware and/or software components could be used in conjunction with computing device 12. Examples, include, but are not limited to: microcode, device drivers, redundant processing units, external disk drive arrays, RAID systems, tape drives, and data archival storage systems, etc.

Aspects of the present invention may be a system, a method, and/or a computer program product. The computer program product may include a computer readable storage medium (or media) having computer readable program instructions thereon for causing a processor to carry out aspects of the various embodiments.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of embodiments of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of embodiments of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to explain the principles of the embodiments, the practical application or technical improvement over technologies found in the marketplace, or to enable others of ordinary skill in the art to understand the embodiments disclosed herein.

The following definitions are specific to this disclosure:

"And/or" is the inclusive disjunction, also known as the logical disjunction and commonly known as the "inclusive or." For example, the phrase "A, B, and/or C," means that at least one of A or B or C is true; and "A, B, and/or C" is only false if each of A and B and C is false.

A "set of" items means there exists one or more items; there must exist at least one item, but there can also be two, three, or more items. A "subset of" items means there exists one or more items within a grouping of items that contain a common characteristic.

"Includes" and any variants (e.g., including, include, etc.) means, unless explicitly noted otherwise, "includes, but is not necessarily limited to."

A "user" or a "subscriber" includes, but is not necessarily limited to: (i) a single individual human; (ii) an artificial intelligence entity with sufficient intelligence to act in the place of a single individual human or more than one human; (iii) a business entity for which actions are being taken by a single individual human or more than one human; and/or (iv) a combination of any one or more related "users" or "subscribers" acting as a single "user" or "subscriber."

The terms "receive," "provide," "send," "input," "output," and "report" should not be taken to indicate or imply, unless otherwise explicitly specified: (i) any particular degree of directness with respect to the relationship between an object and a subject; and/or (ii) a presence or absence of a set of intermediate components, intermediate actions, and/or things interposed between an object and a subject.

A "module" is any set of hardware, firmware, and/or software that operatively works to do a function, without regard to whether the module is: (i) in a single local proximity; (ii) distributed over a wide area; (iii) in a single proximity within a larger piece of software code; (iv) located within a single piece of software code; (v) located in a single storage device, memory, or medium; (vi) mechanically connected; (vii) electrically connected; and/or (viii) connected in data communication. A "sub-module" is a "module" within a "module."

The term "real time" includes any time frame of sufficiently short duration as to provide reasonable response time for information processing as described. Additionally, the term "real time" includes what is commonly termed "near real time," generally any time frame of sufficiently short duration as to provide reasonable response time for on-demand information processing as described (e.g., within a portion of a second or within a few seconds). These terms, while difficult to precisely define, are well understood by those skilled in the art.

The term "causing" or "cause" means that one or more systems (e.g., computing devices) and/or components (e.g., processors) may in in isolation or in combination with other systems and/or components bring about or help bring about a particular result or effect. For example, a server computing device may "cause" a message to be displayed to a user device (e.g., via transmitting a message to the user device) and/or the same user device may "cause" the same message to be displayed (e.g., via a processor that executes instructions and data in a display memory of the user device). Accordingly, one or both systems may in isolation or together "cause" the effect of displaying a message.

The term "computing system" means a single computing device (e.g., a mobile device) and/or multiple computing devices (e.g., multiple cloud computing notes).

The terms first (e.g., first cache), second (e.g., second cache), etc. are not to be construed as denoting or implying order or time sequences. Rather, they are to be construed as distinguishing two or more elements. In some embodiments, the two or more elements, although distinguishable, have the same makeup. For example, a first memory and a second memory may indeed be two separate memories but they both may be RAM devices that have the same storage capacity (e.g., 4 GB).

What is claimed is:

1. A method comprising:
   downloading, in response to a user selection, a health plugin for a behavioral health application installed on the user's mobile device, the selected health plugin configured for use with the behavioral health application in monitoring a first type of health state, the health plugin selected for download from among a plurality of health plugins that are each configured for use with the behavioral health application in monitoring a respective type of health state of a corresponding plurality of types of health states;
   registering, in response to the downloading and based on user health attributes that the selected health plugin is configured to monitor, a plurality of sensor devices to the behavioral health application, wherein the plurality of sensor devices include a microphone and an accelerometer;
   registering, in response to the downloading and based on remedial actions that the selected health plugin is configured to initiate, a plurality of output devices to the behavioral health application, wherein the plurality of output devices include a speaker and a treadmill;
   querying, by the behavioral health application, a health record service for historical data about the user that is associated with the health attributes that the selected health plugin is configured to monitor;
   generating, based on the queried historical data, a Bayesian network configured to utilize a directed acyclic graph to predict triggering causes of health event episodes of the user that are associated with the first type of health state;
   detecting, by the registered plurality of sensor devices, real-time information about the health attributes of the user, wherein the detecting the real-time information includes detecting, by the microphone, a volume level of the user's voice and further includes detecting, by the accelerometer, movements of the user;
   determining, by the behavioral health application and based on the detected information, that a first health event episode is occurring;
   using the Bayesian network to predict a triggering cause of the first health episode;
   selecting, based on the predicted triggering cause, a particular remedial action; and
   initiating, by the behavioral health application, the selected remedial action by activating at least one of the plurality of registered output devices to generate outputs for completing the selected remedial action, wherein the activating the at least one of the plurality of registered devices includes causing the speaker to play a particular song and further includes causing the treadmill to become activated.

* * * * *